United States Patent [19]

Namboodiri et al.

[11] Patent Number: 5,656,447

[45] Date of Patent: Aug. 12, 1997

[54] ANTIBODIES SPECIFIC TO QUINOLINIC ACID

[75] Inventors: M. A. Aryan Namboodiri; John R. Moffett, both of Washington, D.C.

[73] Assignee: Georgetown University, Washington, D.C.

[21] Appl. No.: 99,644

[22] Filed: Jul. 30, 1993

[51] Int. Cl.$^6$ .................................................. G01N 33/53
[52] U.S. Cl. ........................... 435/7.92; 435/7.1; 435/7.95; 435/960; 436/503; 436/512; 436/822; 530/389.1; 530/389.8
[58] Field of Search ............................. 530/389.1, 807, 530/389.2, 389.8; 435/7.92, 7.93, 7.95, 960, 961, 975; 436/547, 528, 531, 822, 503, 512

[56] References Cited

PUBLICATIONS

Moffett et al, 1993, Antibodies to Quinolinic Acid Reveal Localization in Select Immune Cells Rather Than Neurons or Astroglia. Brain Res. 623:337–40.

Moffett et al, 1993. Enhanced Carbodiimide Fixation for Immunohisochemistry: Application to the ... Immunoreactivities in Rat Brain. J. Histochem Cytochem 41:559–570.

Craine, 1991. Antibody Based Assay for Quinolinic Acid. Toxline Crisp Subfile: #Crisp–91–AG09910–01 (Toxicology Res. Proj, NIH).

Goding, 1983. *Monoclonal Antibodies: Principles and Practice*. Academic Press, London. pp. 250–261.

Maurer et al, 1980. Protiens and Polypeptides as Antigens. Meth Enzymol. 70:49–70.

Smith et al, 1983. *Principles of Biochemistry*. McGraw–Hill Book Co., New York. pp. 668–669.

Kohler et al, 1987. Quinolinic Acid Phosphoribosyltransferase: Preferential Glial Localization n the Rat Brain Visualized by Immunocytochemistry. Proc. Natl. Acad Sci USA 84:3491–3495.

Heyes et al, 1992. Poliovirus Induces Indoleamine–2,3–Dioxygenase and Quinolinic Acid Synthesis in Mocaque Brain. FASEB J 6:2977–2989.

Moroni et al, 1984. The Excitotoxin Quinolinic Acid is Present and Unevenly Distributed in the Rat Brain. Brain Res 295:352–355.

Moroni et al, 1984. The Excitotoxin Quinolinic Acid is Present in the Brain of Several Mammals and its Cortical Content Increases During the Aging Process. Neuro Sci Lett. 47:51–55.

Stone et al, 1985. Quinolinic Acid and the Other Kynurenines in the Central Nervous Systems. Neuro Sci 15:597–617.

Shiosaka et al, 1986. A New Method for Producing a Specific and High Titre Antibody Against Glutamate Using Colloidal Gold as a Carrier. Brain Res 382:399–403.

Harlow et al, 1988. *Antibodies: a Laboratory Manual*. Cold Laring Harbor Laboratory. pp. 558, 570–576.

Clinical Neuropharmacology, vol. 7, pp. 448–449, 1984, F.Moroni, et al., "Studies on the Content, Synthesis and Disposition of Quinolinic Acid in Physiology and Pathology".

Neuroscience, vol. 27, No. 1, pp. 49–76, 1988, C.Kholer, et al., "Localization of Quinolinic Acid Metabolizing Enzymes in the Rat Brain. Immunohistochemical Studies Using Antibodies to 3–Hydroxyanthranilic Acid Oxygenase and Quinolinic Acid Phosphoribosyltransferase".

*Primary Examiner*—Christina Y. Chan
*Assistant Examiner*—James L. Grun
*Attorney, Agent, or Firm*—Oblon, Spivak, McClelland, Maier & Neustadt, P.C.

[57] ABSTRACT

Polyclonal antibodies which are specific against quinolinic acid are provided. The antibodies are used for immunohistological detection of quinolinic acid.

16 Claims, 12 Drawing Sheets

FIG. 5A
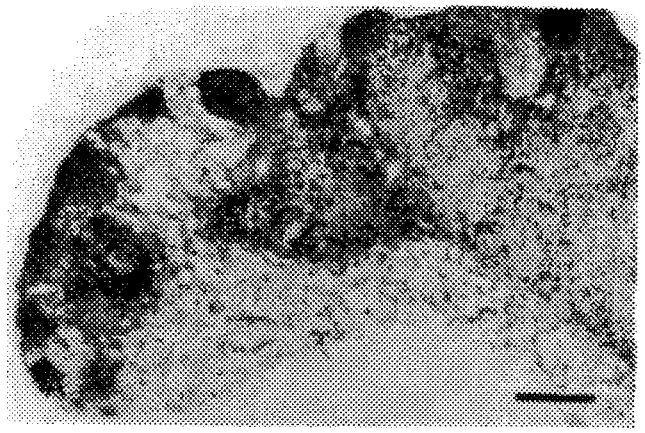
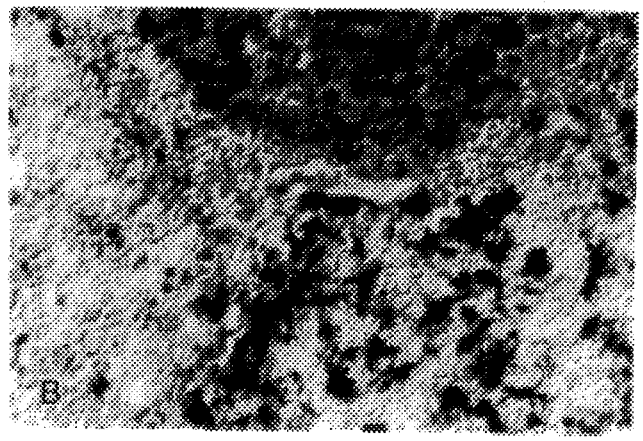
FIG. 5B

FIG. 7A
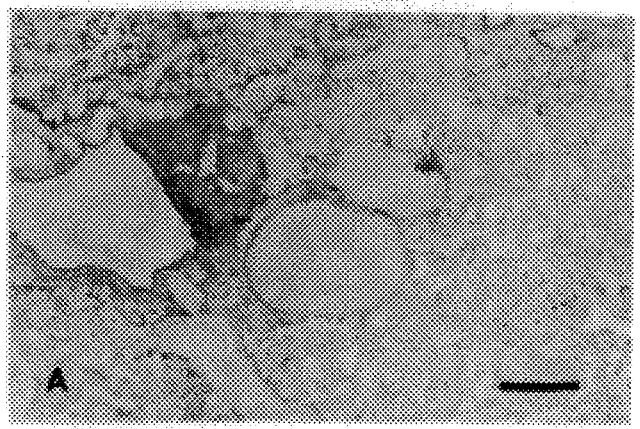
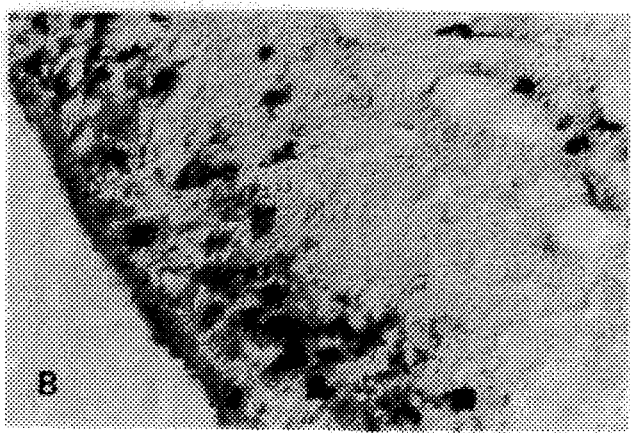
FIG. 7B

ANTIBODIES SPECIFIC TO QUINOLINIC ACID

The work leading to the present invention was supported by NIH Grants EY 09085 and DK 37024. As such, the U.S. government may have certain rights in the present invention.

BACKGROUND OF THE INVENTION

1. Field of the Invention

The present invention relates to antibodies which are specific to quinolinic acid.

2. Description of the Background

Quinolinic acid (QUIN), a metabolite of the kynurenine pathway of tryptophan degradation, is an endogenous neurotoxin which produces excitatory responses in neurons of the mammalian central nervous system. QUIN is produced at an increased rate generally during any physical stress which causes swelling, such as infection, and an increased level of QUIN in the blood or cerebrospinal fluid is indicative of the extent of a particular infection.

Generally, any physical stress causing swelling, including any pathological assault on the body, blunt force injury or even anoxia triggers an increase in QUIN level in blood or cerebrospinal fluid. Studies have indicated that mononuclear phagocytes, and particularly macrophages, produce significant quantities of QUIN.

The excitatory effect produced by QUIN is known to be mediated by the N-methyl-D-aspartate (NMDA) subtype of glutamate receptor. Excessive activation of neuronal NMDA receptors by QUIN and related compounds leads to prolonged calcium influx and eventual neuronal death. When compared with other endogenous excitatory compounds such as glutamate and aspartate, which are only mildly neurotoxic at high concentrations, QUIN is perhaps 100 times more toxic to neurons bearing NMDA receptors.

It is also known that glial cells throughout the central nervous system contain enzymes in the kynurenine pathway of tryptophan metabolism responsible for the synthesis and degradation of QUIN. These cells have been implicated in the production of QUIN in the brain under both normal and pathological conditions.

The concentration of QUIN in the blood, cerebrospinal fluid and brain may become significantly elevated as a result of numerous peripheral and central pathologies. However, it is also known that peritoneal administration of endotoxins increases the level of QUIN in the body, including the brain, to a significant extent.

Although glial cells have been thought to be a source of brain QUIN, it is now considered that there are additional sources. For example, when the central nervous system is under infection by polio virus, increases in the activity of the rate limiting enzyme in the kynurenine pathway, indolamine 2,3-deoxygenase (IDO), can be correlated with increases in QUIN concentration and the severity of central nervous system inflammation.

Further, it has also been reported that compounds released by HIV-I infected microglia are neurotoxic in vitro. This effect is also mediated by the NMDA type of neuronal glutamate receptor.

Additionally, inasmuch as QUIN is a selective NMDA receptor agonist whose systemic and central concentrations are responsive to infection, immune stimulation or damage, QUIN appears to be a significant macrophage/microglia secreted neurotoxin. Although QUIN was not initially detected in neurotoxic supernatants from HIV-I infected mononuclear phagocyte cultures, it was subsequently determined that human macrophages convert tryptophan to QUIN, and at an increased rate under stimulation by γ-interferon or HIV-1 infection in vitro, leading to neurotoxic levels of QUIN in the culture medium. Thus, QUIN appears to be implicated as causative agent of inflammation-mediated excitotoxic neurodegeneration.

Presently, mass spectrometry (MS) is used to detect the concentration of QUIN in a liquid sample. Unfortunately, however, mass spectrometries and gas chromatographs, often used in tandem therewith, are very expensive, and techniques using this equipment are time consuming and require specially trained operators. It would be extremely advantageous if a means were known for performing quantitative analyses of QUIN in fluid samples in a simplified and inexpensive manner.

It would also be quite advantageous if a means were known by which the cellular origins of QUIN could be accurately and rapidly ascertained.

SUMMARY OF THE INVENTION

Accordingly, it is an object of the present invention to provide antibodies which are specific to QUIN.

It is, moreover, an object of the present invention to provide a means for performing quantitative analyses of QUIN in fluid samples in a simplified and inexpensive manner.

It is also an object of the present invention to provide a method for detecting or assessing the severity of infections, including, but not exclusively, neurodegenerative diseases using the antibodies of the present invention.

It is, moreover, an object of the present invention to neutralize or minimize the neurotoxicity of QUIN in mammals.

Further, it is an object of the present invention to provide a means of immunohistochemically analyzing both neural and non-neural fixed tissues.

Accordingly, the above objects and others are provided by polyclonal antibodies which are highly specific against QUIN.

BRIEF DESCRIPTION OF THE DRAWINGS

FIG. 5A shows that cells which stained strongly for QUIN were observed throughout the lymph nodes. Bar=500 µm.

FIG. 5B illustrates that cortical B-cell nodules contained a high degree of diffuse QUIN immunoreactivity, while staining in T-cell parafollicular areas was discretely localized to macrophage-like and dendritic-like cells. Bar=500 µm.

FIG. 7A illustrates QUIN immunoreactivity in a population of small, round cells located in an around the alveoli of rat lung tissue. Bar=500 µm.

FIG. 7B illustrates that numerous immunoreactive cells with ramified morphology were observed in the bronchus-associated lymphoid tissue (BALT). Bar=500 µm.

DETAILED DESCRIPTION OF THE PREFERRED EMBODIMENTS

Figure 1:
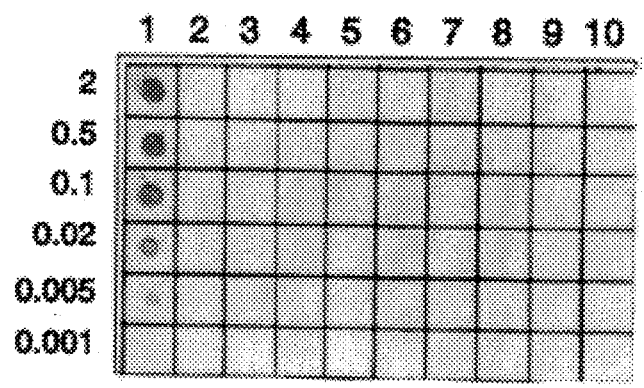
FIG. 1 illustrates specificity testing of purified antibodies to quinolinic acid by dot-blot assay. Protein samples, with various molecules coupled to them by carbodiimide reaction, were spotted on nitrocellulose sheets in decreasing concentrations. The protein concentrations ranged from 2 μg to 0.001 μg (1 ng) per spot. The small molecules coupled to the proteins were, from left to right, 1) quinolinic acid (QUIN), 2) picolinic acid, 3) nicotinic acid, 4) kynurenic acid, 5) guinaldic acid, 6) xanthurenic acid, 7) glutamate, 8) gamma amino butyric acid, and 9) tryptophan coupled to BSA, and 10) glutamate coupled to soluble rat brain proteins.

In accordance with the present invention, it has been surprisingly discovered that antibodies which are specific against QUIN can be provided. The antibodies of the present invention may, thus, be advantageously used to minimize, or even neutralize, neurotoxicity of QUIN in mammals. These antibodies may also be used to perform quantitative analyses of QUIN in fluid samples in a simplified and inexpensive manner. Generally, the present antibodies can be produced by producing protein-coupled QUIN and gold-particle-adsorbed QUIN and injecting the same into a host animal. Further, the antibodies produced may be purified by conventional methodologies, for example, by nitrocellose-based reverse affinity absorption.

The present invention is quite advantageous inasmuch as the antibodies provided against QUIN greatly simplify and reduce the cost of performing quantitative analyses of the QUIN content of blood and other fluid samples by using ELISA and RIA type assays. Further, the present antibodies may be used in diagnostic test kits which may be used in hospitals and clinics to rapidly assess the degree of a suspected neurodegenerative infection. The present antibodies may, moreover, be used for determining the degree of infiltration of active macrophages into a biopsy specimen.

In accordance with the present invention, polyclonal antibodies which bind specifically to quinolinic acid are provided, permitting for the first time the histopathological detection of cells which produce this neurotoxic compound. Quinolinic acid is only made in significant amounts in the body when inflammation occurs, and the level in blood and body tissues is proportional to the number of immune cells which have been activated. Because quinolinic acid is produced during all inflammatory processes, the present rapid, economical and simple method of detecting quinolinic acid in tissue and body fluid samples is of great diagnostic value. Further, because quinolinic acid is produced during an infection by only certain types of immune cells, namely macrophages and dendritic cells, antibodies to protein-fixed QUIN afford a histopathological reagent for use in biopsy analysis and basic research.

Neurodegenerative disorders that involve inflammatory processes, including stroke, brain damage, brain or meningeal infections, AIDS dementia complex, Alzheimer's disease, and many others, lead to the release of QUIN in the brain. As such, the present antibodies against quinolinic acid are of great importance in determining the cause and location of overproduction of this neurotoxic compound, as well as for providing means for reducing the concentration of quinolinic acid under certain conditions.

The production of the present antibodies will now be generally described.

In general, the present polyclonal antibodies may be produced by raising the same against either protein-coupled QUIN or gold-particle adsorbed QUIN.

For example, QUIN-hapten may be rendered immunogenic by conjugation with peptides and proteins as described in U.S. Pat. Nos. 5,639,512; 4,461,761 and 4,812,554, each of which are incorporated herein in the entirety.

Furthermore, gold-particle adsorbed QUIN may be produced using the procedure described by Shiosaki, S. et al in *Brain Research*, 382 (1986) 399–403. Generally, the procedures described therein may be used using, however, QUIN as the hapten.

The production of the present antibodies will now be described in more detail in the following Example, which is provided solely, as all Examples herein, for purposes of illustration and is not limitative thereof.

EXAMPLE 1

Antibody Preparation and Tissue Preparation

Reagents were purchased from Sigma (Rockford Ill.), immunochemicals from Vector (Burlingame Calif.), and animals were acquired from Zivic-Miller (Allison Park Pa.). Tissue preparation was in accordance with the procedure described by Moffett et al, *Journal of Histochemistry and Cytochemistry*, vol. 41, No. 4, pp. 559–570 (1993) and *Methods in Enzymology*, vol. 70, "Immunological Techniques", pp. 151–165 (1980), Bauminger, S. et al.

Antibody Production

A New Zealand white rabbit was immunized on a tri-monthly schedule with alternating injections of protein conjugated quinolinic acid and gold particle adsorbed quinolinic acid was prepared by adding 2 mg of quinolinic acid to 500μ of a colloidal gold solution (15 nM particle size; EY Lab., San Mateo Calif.). The mixture was emulsified with 1 ml of Freund's incomplete adjuvant (Gibco Lab., Grand Island N.Y.) and injected subcutaneously at multiple sites. Blood was collected from the rabbit 8–10 days after each injection.

Protein conjugated quinolinic acid was prepared by adding 10 mg of quinolinic acid and 10 mg of either Limulus hemocyanin or Bovine thyroglobulin to 10 ml of purified water. The pH was adjusted to 6.5 with NaOH. Two hundred milligrams of carbodiimide were added to the mixture, and the solution was mixed for 1 hour at room temperature. The solution was dialyzed against 10 mM phosphate buffered saline (PBS, pH 7.4) and stored frozen until used. For injections, 1 ml of the protein solution was emulsified with 1 ml of Freunds adjuvant and the emulsion was injected subcutaneously at multiple sites.

Tissue Preparation

Six albino Sprague-Dawley rats, weighing between 120 and 160 grams, were deeply anesthetized with nembutal and perfused transcardially with 400 ml of a 37° C. aqueous solution of 6% 1-ethyl-3(3-dimethylaminopropyl) carbodiimide hydrochloride, 5% DMSO and 1 mM N-hydroxysuccinimide as previously described (Moffett et al., 1993). Brain and other tissues were postfixed in 5% formaldehyde and cryoprotected by passage through 10%, 20%, and 30% sucrose prior to freezing. Blocks of tissue were coated with O.C.T. compound (Miles, Elkhart Ind.) and frozen with compressed gas. Brains were sectioned in the frontal (5) and horizontal (1) planes, while spleen, thymus, liver, intestine, lymph node, skin and lung were cut in cross-section, at a thickness of 20 microns.

Hapten-protein conjugate synthesis

Eight hapten-protein conjugates, used for improving and testing antibody specificity, and for blocking studies, were prepared with crystalline bovine serum albumin (BSA) as follows. For each conjugate, 20 mg of BSA was added to 10 ml water. Quinolinic, picolinic, nicotinic, xanthurenic, quinaldic, kynurenic, gamma amino butyric and glutamic acids, and tryptophan, were added to separate tubes to a final concentration of 10 mM. The solutions were adjusted to approximately pH 6.5 with NaOH where necessary. Two hundred milligrams of carbodiimide were added to each, and the tubes were rotated for 1 hour at room temperature. The conjugates were dialyzed against 100 mM PBS at pH 8 and stored with 0.1% sodium azide at 4° C. Nitrocellulose strips containing adsorbed protein conjugates were produced by treating 10 8 mm×80 mm pieces of nitrocellulose (Bio Rad, Richmond Calif.) with 10 ml of a solution containing 200 μg/ml of a given protein conjugate. The strips were agitated in the solutions by rotation in polypropylene tubes for 2 hours at room temperature, and then treated with 2 changes of 4% NGS. The strips were stored at 4° C. in 2% NGS.

Brain protein preparation

A male albino rat weighing 120 gm was deeply anesthetized with Nembutal, decapitated, and the brain quickly removed and placed in 20 ml ice cold artificial cerebrospinal fluid. The brain was homogenized with a polytron and centrifuged ad 48,000×g for 10 min at 4° C. The supernatant was removed and frozen while the pellet was homogenized in 20 ml of 6M quanidine HCl. The pellet and supernatant fractions were extensively dialyzed against PBS and the supernatant was frozen again. The pellet fraction was homogenized in 20 ml of 10 mM PBS with 2% Triton X-100 and centrifuged at 48,000×g for 20 min at 4° C. The remaining pellet was discarded and the solubilized pellet proteins were dialyzed extensively against PBS and stored frozen. Several types of conjugates were produced with the brain protein extracts. The first type was produced by diluting the extracts 1:10 in purified water and treating them with 20 mg/ml of carbodiimide for 1 hour at room temperature. Additional brain protein aliquots, diluted 1:10, were mixed with 1 mg/ml of either quinolinic, picolinic, nicotinic or glutamic acids, and the pH of the solutions was adjusted to 6.5 with NaOH. The mixtures were coupled by treating them with 20 mg/ml of carbodiimide for 1 hour at room temperature. Ad additional protein-hapten conjugate was produced with the soluble brain protein extract and 4 small molecules combined; glutamate, aspartate, gamma amino butyric acid and picolinic acid. A solution was prepared with 9 ml of purified water, 1 ml of the soluble brain protein fraction, 2 mg of each small molecule and 200 mg of carbodiimide. The solution was adjusted to pH 6.5 with NaOH, rotated for 1 hour at room temperature. All conjugates were dialyzed extensively against 100 mM PBS (pH 8) and stored with 0.1% sodium azide at 4° C. Nitrocellulose strips were prepared with the brain protein conjugates as described for BSA conjugates above.

Affinity purification of quinolinate antibodies

Quinolinic acid-coupled aminoalkyl-agarose gels were prepared by mixing 7 ml of gel slurry (Affi-gel 102; Bio-Rad, Richmond Calif.) with 50 mg of quinolinic acid, and the pH was adjusted to 6.5 with NaOH. Four hundred milligrams of carbodiimide, dissolved in 3 ml of water, were added to the slurry, and the mixture was mixed by rotation for 2 hours at room temperature. The slurry was packed in a 1 cm×10 cm column, washed thoroughly with 10 mM PBS, and treated for 30 minutes with 2% normal goat serum in PBS containing 0.1% sodium azide (2% NGS).

One milliliter of crude antisera was diluted 10 fold in 2% NGS. The solution was applied to the column containing the affinity matrix, and the mixture was continuously circulated with a peristaltic pump for 18 hours at room temperature. The column was eluted with 50 ml of 6M guanidine HCl, 1 ml of normal goat serum was added, and the eluate was dialyzed thoroughly against PBS. All purified antibodies were stored in 2% NGS at 4° C.

Antibody adsorption purification

Both affinity purified and crude antisera were subjected to adsorption purification with nitrocellulose immobilized protein conjugates. Antibody solutions, starting from 1 ml of crude serum, were diluted 1:50 in 4% NGS. Affinity purified antibodies were incubated overnight, using rotational agitation, with 600 μg of each of the immobilized protein-hapten conjugates of picolinic, nicotinic and glutamic acids, plus 6 nitrocellulose strips coated with carbodiimide treated brain proteins. The crude serum was adsorption purified by preincubation with 1.2 mg each of immobilized picolinic, nicotinic, glutamic and gamma-amino butyric acids, and with 400 μg each of aspartate, sryptophan and serotonin conjugates of BSA. In addition, the 50 ml solution of adsorption purified antibodies was preincubated with 12 nitrocellulose strips coated with carbodiimide treated brain proteins. After preadsorption, the antibody solutions were filtered through 0.8 μm filters, and stored at 4° C. A similar purification was achieved by using 4 nitrocellulose strips containing the brain proteins coupled with multiple small molecules simultaneously (glutamate, aspartate, gamma amino butyric acid and picolinic acid), and one strip each of tryptophan-BSA, glutamate-BSA and carbodiimide-treated brain protein.

Specificity testing

Antibody specificity testing was done with nitrocellulose sheets spotted with a range of concentrations of all of the hapten-BSA conjugates described above. Individual spots ranged in protein content from 2 µg to 1 ng. Carbodiimide-treated brain proteins, with and without quinolinic acid coupled to them, were tested without further dilution. Affinity purified antibodies were diluted 1:300, while the adsorption purified antibodies were diluted 1:10,000 in 2% NGS. Antigen test sheets were incubated overnight with primary antibody at room temperature with constant rotary agitation and washed 6 times with PBS for 2 minutes each time. The bound antibody was visualized by incubating the sheets for 60–90 minutes with horseradish peroxidase labeled goat anti-rabbit secondary antibodies (Kirkegaard and Perry, Gaithersburg Md.). The sheets were washed thoroughly and developed with diaminobenzidine and urea peroxide (Sigmafast tablets).

Immunohistochemistry

Immunohistochemistry was performed by the floating section and on-slide techniques. To inhibit endogenous peroxidase activity, tissue sections were incubated with 0.3% $H_2O_2$ in methanol for 30 minutes, washed with PBS, and treated with 2% NGS. Affinity/adsorption purified antibodies, diluted 1:300, or adsorption-only purified antibodies diluted 1:5000 to 1:12,000 in 2% NGS, were incubated with tissue sections overnight at room temperature with constant rotary agitation. Bound antibodies were visualized by the avidin-biotin complex method (Vectastain Elite). Tissue sections were incubated with the secondary biotinylated antibody and avidin-biotin-peroxidase solutions for 60 to 90 minutes each, and developed with diaminobenzidine and urea peroxide.

Antibody blocking studies

Quinolinic acid mediated blocking of antibody binding to tissue was tested by incubating the working dilutions of primary antibody with various combinations of conjugate-adsorbed nitrocellulose strips. Primary antibodies were diluted 1:10,000 in 2% NGS relative to the volume of crude serum. Protein conjugates of picolinc, glutamic, xanthurenic, and kynurenic acids and tryptophan were pre-incubated with primary antibody solutions a concentration of approximately 50 µg of conjugate per ml of dilute antibody (2.5 strips in 10 ml of antibody). Another aliquot of the same volume of dilute primary antibody was treated with 10 times less nitrocellulose, containing protein coupled quinolinic acid (0.25 strips or approximately 5 µg/ml of adsorbed protein). The solutions were incubated overnight at room temperature with constant rotation before applying to carbodiimide fixed tissue sections of spleen and thymus.

Antibody Binding Specificity to Hapten-Protein Conjugates

Affinity and adsorption purified antibodies were tested against nitrocellulose immobilized protein conjugates of a number of small molecules.

The antibodies were also tested against carbodiimide treated brain proteins, glutamate-coupled brain proteins, and a mixture of molecules coupled to brain proteins. After preadsorption of the affinity purified antibodies with picolinic, nicotinic and glutamic acid conjugates of BSA, less than 1% cross-reactivity was observed with the other small molecules coupled to BSA. Preferably, however, less than 0.25% cross-reactivity is observed with these other small molecules. Under these conditions, the antibody clearly labeled spots of BSA conjugated quinolinic acid containing 5 ng of protein. The antisera which were purified by adsorption with nitrocellulose immobilized protein conjugates alone were superior to the antisera which were first affinity purified before adsorption. The resultant antibodies could be diluted 30–40 times further, and exhibited a greater signal to noise ration. No cross reactivity was observed with any of the conjugates, or brain proteins, using the adsorption purified antibodies at their working dilutions.

Quinolinic acid immunoreactivity in the rat brain

Figure 2:
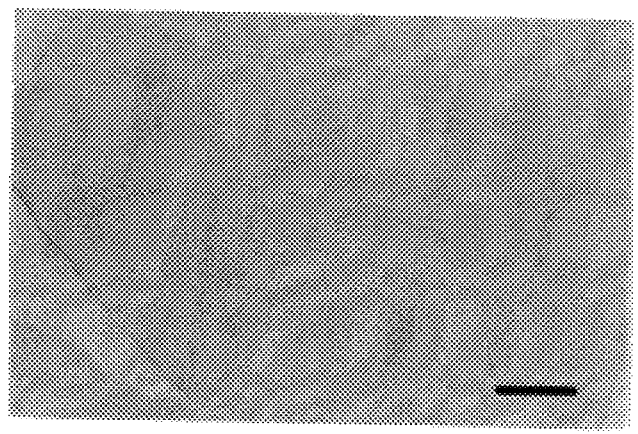
FIG. 2 illustrates QUIN immunoreactivity in carbodiimide fixed rat brain tissue. No QUIN immunoreactivity can be seen in this horizontal section of rat hippocampus stained with polyclonal anti-quinolate antibodies.

Quinolinic acid immunoreactivity was not consistently observed in normal rat brain tissue (FIG. 2). In FIG. 2, virtually no QUIN immunoreactivity can be seen in this horizontal section of rat hippocampus, stained with polyclonal anti-QUIN antibodies diluted 1:5,000. Bar=250 µm. Faint immunoreactivity was observed in the ventricular system, e.g., along the lateral border of the lateral ventricle. Mild immunoreactivity was also observed in circumventricular organs, choroid plexus and meninges. No quinolinic acid immunoreactivity was observed in neurons, astroglia, oligodendrocytes, microglia or fiber pathways.

Immunoreactivity in spleen

Figure 3A:
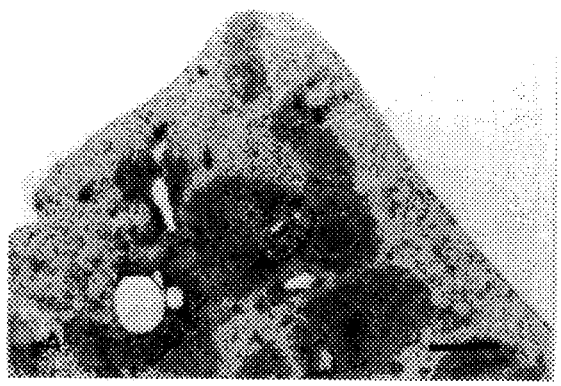
FIG. 3A illustrates QUIN immunoreactivity in carbodiimide fixed rat spleen tissue and shows that immunoreactivity of polyclonal anti-QUIN antibodies could not be blocked or reduced by pretreatment overnight with a conjugate of tryptophan-BSA in excess of 50 μg/ml.
Figure 3B:
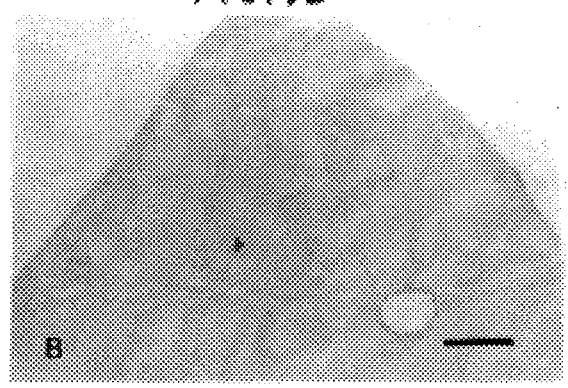
FIG. 3B illustrates that QUIN immunoreactivity was eliminated by incubation of the dilute primary antisera with 5 μg/ml of QUIN conjugated BSA adsorbed to nitrocellulose.
Figure 3C:
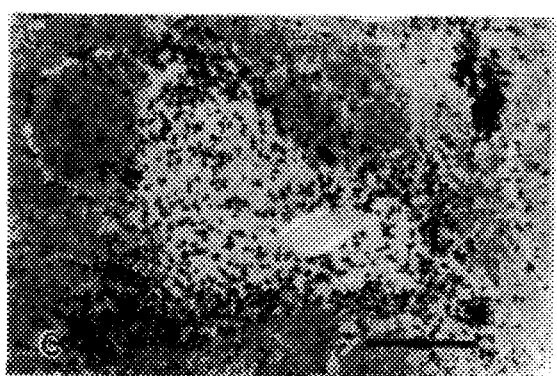
FIG. 3C illustrates immunoreactive cells which were observed in the highest numbers in periarterial lymphocyte sheaths (PALS), and tended to occur in clusters concentrated toward the edges of T-cell regions.
Figure 3D:
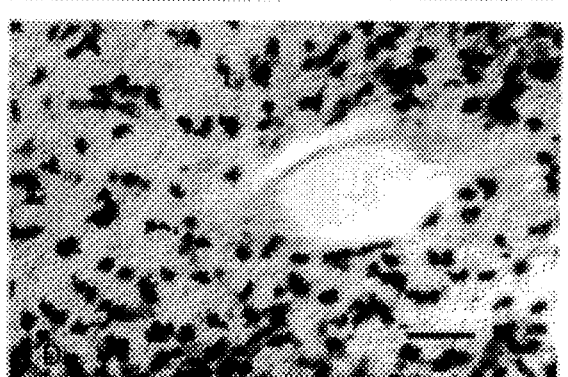
FIG. 3D illustrates follicular marginal zones appearing as unstained circular strips near the perimeter of the mildly stained follicals, and containing variable numbers of heavily stained macrophage like cells.

When carbodiimide fixed rat spleen was sectioned and stained with the affinity purified and/or preadsorbed antibodies, the appearance of strong quinolinic acid immunoreactivity was observed in a population of cells throughout the spleen (FIGS. 3A, 3C, 3D). The distribution and number of strongly stained cells was variable from one animal to another. Large numbers of clustered and densely packed immunoreactive cells were seen in some spleens, while others displayed a more scattered distribution of stained cells. Generally, immunoreactive cells were observed in the highest numbers in periarterial lymphocyte sheaths (PALS), and tended to occur in clusters concentrated toward the edges of T-cell regions (FIG. 3C). Light to moderate, uniform, diffuse staining occurred within all B-lymphocyte follicles, defining them from the surrounding spleen tissue, since no immunoreactivity occurred in the small cells within either T-cell regions, or within the red pulp. Follicular marginal zones appeared as unstained circular strips near the perimeter of the mildly stained follicles, and contained variable numbers of heavily stained macrophage-like cells (FIG. 3D). Scattered, strongly immunoreactive cells were observed throughout the red pulp, but at a significantly lower density than in the T-cell PALS. Occasional clusters of diffusely stained cells were observed within some follicular germinal centers. All quinolinate immunoreactivity was eliminated by incubation of the dilute primary antisera with 5 µg/ml of quinolinic acid conjugated BSA adsorbed to nitrocellulose (FIG. 3B). The immunoreactivity could not be blocked or reduced with the other conjugates in excess of 50 µg/ml (FIG. 3A).

Quinolinic acid immunoreactivity in thymus

Figure 4A:
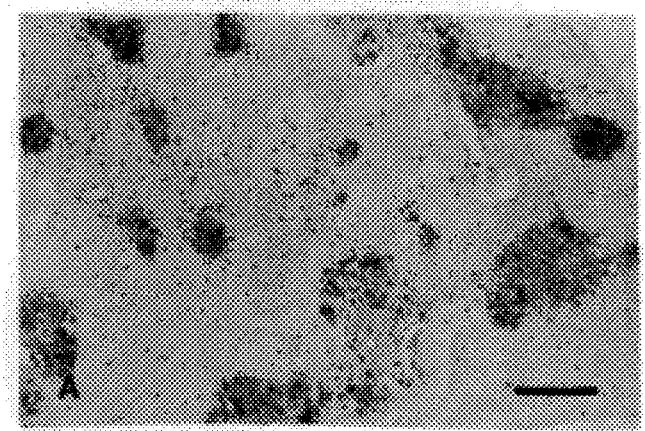
FIG. 4A illustrates QUIN immunoreactivity in rat thymus, where round cells were stained only infrequently in the cortex. Bar=500 µm.
Figure 4B:
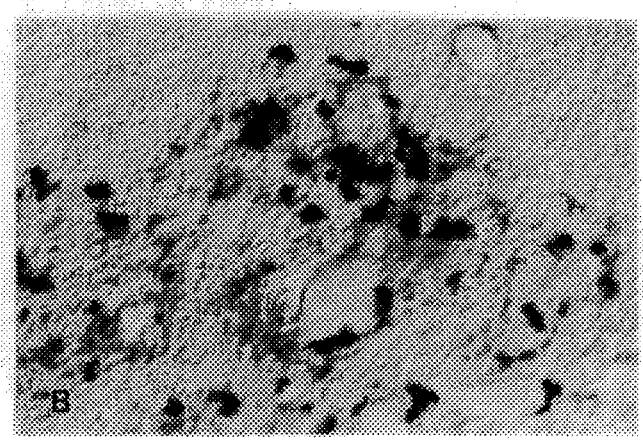
FIG. 4B also illustrates QUIN immunoreactivity in rat thymus, where round cells were stained only infrequently in the cortex. Bar=50 µm.

Strong quinolinate immunoreactivity in the thymus was observed in a morphologically heterogenous group of cells located in the medulla (FIGS. 4A–4B). Mild but clear staining was observed in a population of cells that was more highly ramified and larger in size than the strongly stained cells. These were morphologically reminiscent of dendritic cells. Scattered, relatively round cells, were observed in relatively low number in the thymic cortex. Very light, nonuniform, diffuse staining was observed in the medulla, but no immunoreactivity was observed in the small cortical cells. In FIGS. 4A–4B, numerous cells with highly variable morphology were observed throughout the medulla of the thymus. Only infrequent round cells were stained in the cortex. Bar=500 μm(FIG. 4A), 50 μm(FIG. 4B).

Quinolinate staining in lymph nodes

Similar to the case of the spleen, many strongly immunoreactive cells were observed in lymph nodes, particularly in the mesenteric lymph nodes (FIGS. 5A–5B). Similar to the spleen, the cells were approximately 15 μm in diameter, and were highly variable in morphology. Strongly quinolinate positive cells were preferentially located in the perifollicular and deep cortex, or T-cell enriched regions of the lymph node. The most immunoreactive cells appeared morphologically to be macrophages and dendritic cells. Stronger diffuse staining was observed in the B-cell follicles of mesenteric lymph nodes than in those of the spleen, and in many follicles, an increased staining of B-cell germinal centers was observed. The staining within B-cell regions was not clearly localized to the cellular or extracellular compartment.

In FIG. 5A, cells which stained strongly for quinolinic acid were observed throughout the nodes. Cortical B-cell nodules contained a high degree of diffuse immunoreactivity, while staining in T-cell parafollicular areas was discretely localized to macrophage-like and dendritic-like cells (FIG. 5B). Bar=500 μm(FIG. 5A), 50 μm(FIG. 5B).

Immunoreactivity in rat liver

Figure 6:
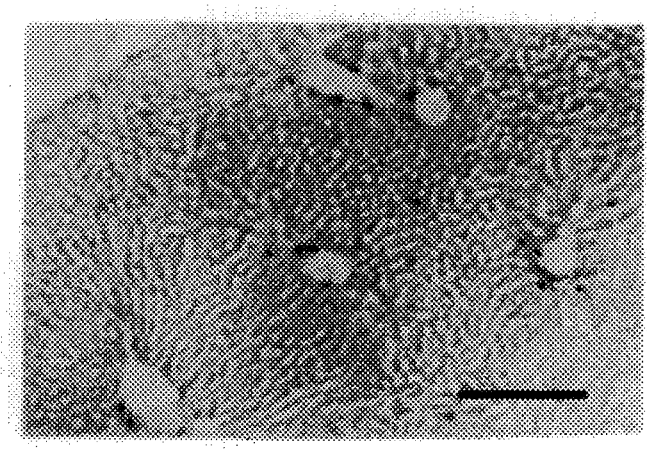
FIG. 6 illustrates carbodiimide fixed rat liver tissue stained for QUIN, and that only widely scattered, round, perivascular cells were observed to be QUIN positive in normal rat liver.

Immunoreactivity in the liver was very limited, and confined to scattered, intensely stained round cells, 10–15 μm in diameter, in and around the vasculature (FIG. 6). No staining was observed in any other cell type in normal rat liver.

In FIG. 6, only widely scattered, round, perivascular cells were observed to be QUIN-positive in normal rat liver. Bar=200 μm.

Lung tissue stained for quinolinic acid. Small, round, scattered immunoreactive cells were observed within the vasculature and alveoli of lung tissue (FIG. 7). Numerous immunoreactive cells with ramified morphology were observed in the bronchus-associated lymphoid tissue (BALT). These cells were often concentrated below the dome epithelium lining the airways (FIG. 7B). The great majority of cells in the lung of control rats were unstained.

In FIG. 7A, immunoreactivity was observed in a population of small, round cells located in and around the alveoli. Additionally, larger cells with complex morphology were observed at the periphery of BALT, usually below the dome epithelium (FIG. 7B). Bar=500 μm (FIG. 7A), 50 μm (FIG. 7B).

Figure 8A:
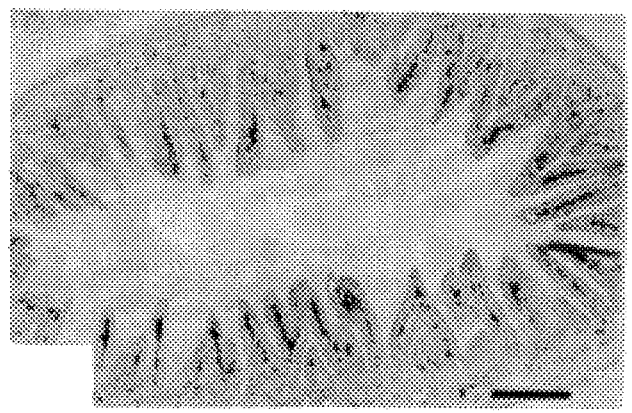
FIG. 8A illustrates results obtained from rat intestine tissue and shows that numerous immunoreactive cells were observed in the small intestine. Bar=500 µm.
Figure 8B:
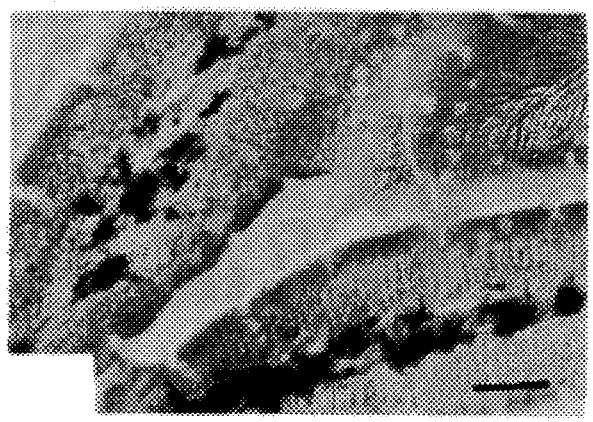
FIG. 8B illustrates that numerous immunoreactive cells were observed within the lamina propria of the mucosal villi. Bar=500 µm.
Figure 8C:
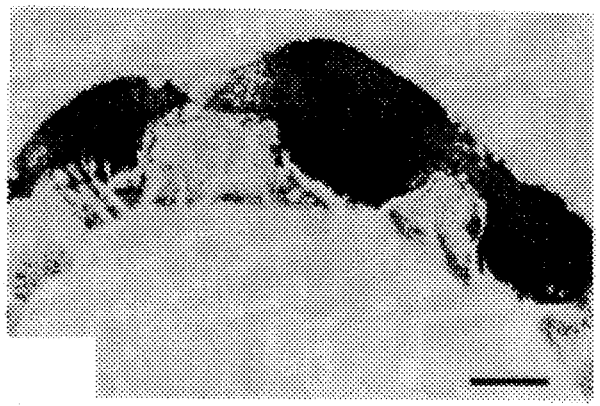
FIGS. 8C and 8D illustrate intense QUIN imunoreactivity in the gut-associated lymphoid tissue (GALT). Bar=500 µm and 200 µm, respectively.
Figure 8D:
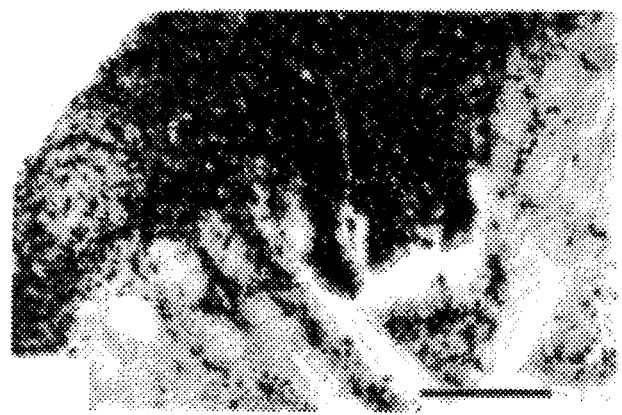
Figure 8E:
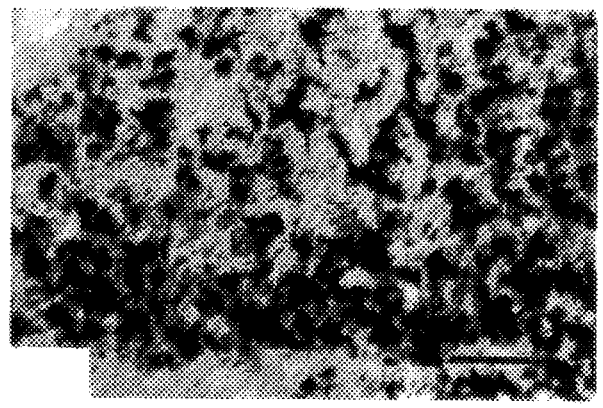
FIG. 8E illustrates that T-cell areas contained strongly immunoreactive cells with the morphology of macrophages and dendritic cells. Bar=50 µm.
Figure 8F:
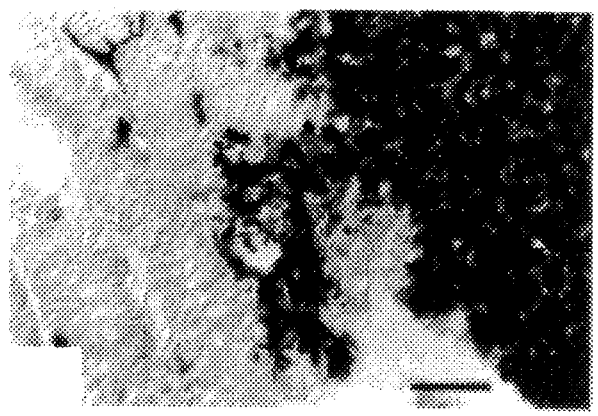
FIG. 8F illustrates that a cell with the morphology of a dendritic cell can be seen in an intestinal villus, adjacent to a B-cell follicle. Bar=50 µm.

In FIGS. 8A–8B, scattered cells throughout the lamina propria of intestinal villi were moderately to strongly stained. The staining in gut-associated lymphoid tissue was among the strongest observed in any lymphoid organ, with staining in B-cell follicles being intense throughout (FIGS. 8C, 8D, 8F). T-cell areas contained strongly immunoreactive cells with the morphology of macrophages and dendritic cells, similar to the pattern observed in the T-cell areas of other lymphatic structures (FIG. 8E). A cell with the morphology of a dendritic cell can be seen in an intestinal villus, adjacent to a B-cell follicle (FIG. 8F). Bar=500 μm (FIGS. 8A, 8C), 50 μm (FIGS. 8B, 8E, 8F), 200 μm (FIG. 8D).

Quinolinate positive cells in small intestine

Numerous immunoreactive cells were observed in the small intestine (FIG. 8A), located within the lamina propria of the mucosal villi (FIG. 8B). Very intense quinolinic acid immunoreactivity was observed in the gut-associated lymphoid tissue (GALT) FIG. 8C). As in the case of spleen, thymus, and lymph node, very strong immunoreactivity was observed in a population of morphologically diverse cells in the T-cell enriched interfollicular cortex (FIG. 8E). These cells appeared morphologically to be both macrophages and dendritic cells. Compared with spleen and lymph node, however, the diffuse staining in B-cell follicles within the GALT was substantially more intense (FIGS. 8C, 8D, 8F). A population of scattered macrophage-like cells deep within the follicles, and similar subepithelial cells in regions where the follicles reach the mucosal surface, where the most immunoreactive cells in GALT nodules. The remainder of the smaller, round cells in the follicles appeared diffusely, but relatively strongly, stained.

Quinolinic acid in skin tissue

Figure 9A:
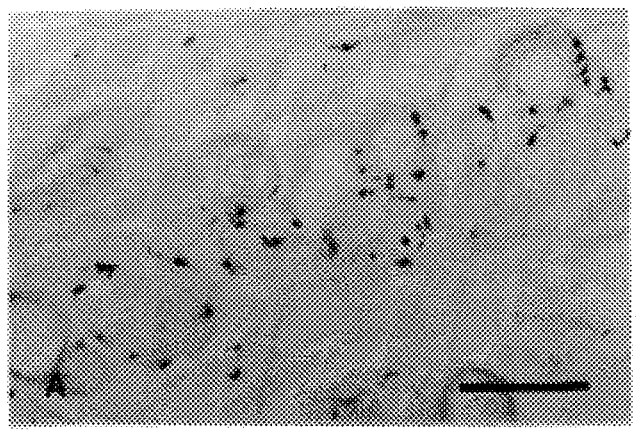
FIGS. 9A and 9B both illustrate QUIN immunoreactivity in the tail skin of the rat.
Figure 9B:
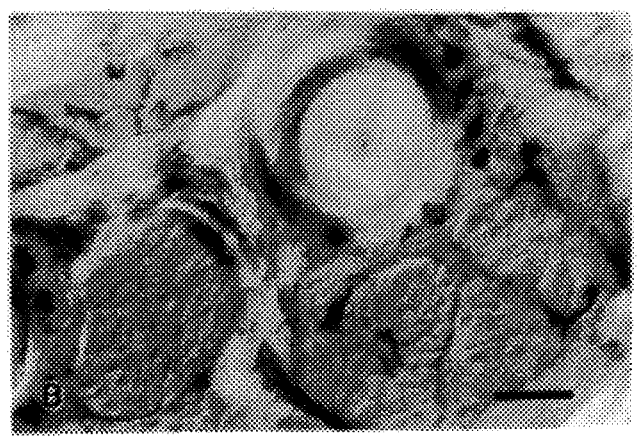

Scattered cells with highly complex morphology were moderately stained in the tail skin of the rat. These cells appeared morphologically to be Langerhans cells, and were located mainly within the hair follicles and sebaceous glands, although some were noted in the epidermis (FIGS. 9A–9B).

The production of highly specific antibodies to quinolinic acid, and their use in the immunohistochemical localization of this endogenous neurotoxin in cells of the immune system, demonstrates the utility of the carbodiimide method for determining the cellular localization of small molecules, particularly those lacking primary amine groups (Moffett et al, 1993). The present study was undertaken to delineate which of the two proposed cell types; astrocytes or mononuclear phagocytes, produce quinolinic acid under normal (control) conditions. The results indicate that quinolinic acid is normally produced only by cells of the immune system with the morphological and anatomical characteristics of macrophages and dendritic cells. Additional staining was associated with B-cell follicles in all lymphoid organs, but this staining was not clearly associated with specific cells. These findings do not preclude the possibility that other cell types, such as astrocytes, produce quinolinic acid under pathological conditions. However, the evidence available to date strongly implicates mononuclear phagocytes in the synthesis and release of quinolinic acid. Studies to determine the cell types which produce quinolinic acid in the brain under pathological conditions are underway in our laboratory.

Increases in quinolinic acid concentrations in the blood and brain result from widely disparate pathological phenomena. It is becoming increasingly apparent that a primary common factor in these diverse processes is the activation of macrophages, and possibly CNS microglia. Interferon-γ is the most effective inducer of IDO, the initial rate-limiting enzyme in the kynurenine pathway of tryptophan degradation. The functional significance of interferon-γ induced degradation of tryptophan by macrophages has been a mystery for over a decade. Activation of IDO is the specific mechanism involved, but the role of this enzyme in macrophages is not clear. IDO is a potent oxygen radical scavenger which could protect these cells from their own reactive oxygen products. However, no other significant role in the activation of mononuclear phagocytes has been elucidated. One proposal for the functional role of IDO activation by interferon-γ in macrophages involves a compound which is metabolically and structurally similar to quinolinic acid. Picolinic acid is also a product of the kynurenine metabolic pathway, and has been proposed to be a second, possibly autocrine, signal which acts in conjunction with interferon-γ to activate macrophages. Such a role for quinolinic acid would also be consistent with its observed localization in the immune system, suggesting that quinolinic acid, rather than picolinic acid, may serve this function in vivo.

Compounds released by HIV-1 infected microglia are neurotoxic, and this effect is mediated by the NMDA type of glutamate receptor. The compounds directly responsible for the cytoxic activity of mononuclear phagocytes are unknown, but many compounds have been implicated. These include nitric oxide, highly reactive oxides including $H_2O_2$ and superoxide anion, and glutamate. However, it has been demonstrated that macrophage induced cytotoxicity in NMDA receptor bearing neurons is mediated by the NMDA receptor, not by reactive intermediates or cytokines. Because quinolinic acid is a selective NMDA receptor agonist whose systemic and central concentrations are responsive to infection, immune stimulation, or damage, it represents a significant candidate as a macrophage/microglia secreted neurotoxin. However, initial reports failed to detect quinolinic acid in neurotoxic supernatants for HIV-1 infected mononuclear phagocyte cultures. Subsequently, human macrophages were found to convert tryptophan to quinolinate, and to substantially increase the rate of conversion when stimulated with interferon-γ (Heyes et al., 1992e). The identification of high levels of quinolinic acid in stimulated macrophage culture supernatants suggests that quinolinic acid should be reexamined as a possible causative agent in excitotoxic neurodegeneration.

The quinolinic acid staining observed within the immune system was consistent with localization to a subset of macrophages and dendritic cells. A diffuse staining was also observed in many B-cell follicles in all lymphoid organs, but this immunoreactivity was not clearly associated with any cell type. In normal rats, with no overt signs of infection, no immunoreactivity was observed in resting microglia, or in macrophages within the brain vasculature. However, many apparent macrophages were quinolinate positive in spleen, thymus, lymph node, GALT and BALT. In addition to macrophages, other cell types, such as dendritic cells (e.g., interdigitating cells and Langerhans cells), were apparent in areas such as thymus medulla, spleen T-cell PALS, or perifollicular cortex, and skin. Localization to macrophages and dendritic cells could imply that quinolinic acid plays a functional role in phagocytosis, antigen processing or antigen presentation. The immunoreactivity observed in spleen, thymus, lymph node, and GALT was also suggestive of a specific interaction between quinolinic acid positive cells and lymphocytes, including both T-cells and B-cells. The strongest immunoreactivity observed in spleen, thymus, and lymph node was always seen in a population of macrophage-like and dendritic-like cells in T-cell regions, concentrated at the periphery of the T-cell zone. This finding is congruous with the reported induction of IDO in mononuclear phagocytes by interferon-γ. Activated T-cells release interferon-γ which would activate local macrophages, including the induction of IDO activity. The quinolinic acid produced and released by the activated macrophages might then act back on T-cells, or other cells in the immune system, such as B-cells. The diffuse staining in the B-cell follicles of all lymphoid tissues was indeterminate, i.e., it could not be conclusively associated with specific cells. It was not clear whether this staining was intracellular within B-cells, or was present extracellularly within B-cell follicles. However, this staining in B-cell follicles, and to a greater extent in some germinal centers, was the only observed quinolinic acid immunoreactivity that was not readily definable as intracellular. This could suggest that macrophages which are activated by interferon-65 in T-cell regions, then migrate to B-cell follicles where they release quinolinic acid.

One possibility suggested by these findings is that quinolinic acid may act as a cytokine, or signalling substance, which is only synthesized and released by macrophages, dendritic cells, etc. in response to stimulation. The possibility that quinolinate is a cytokine would explain the observed dramatic increase in tryptophan degradation via kynurenine pathway metabolism in activated mononuclear phagocytes. If this proves correct, then only those mononuclear cells in which IDO induction had occurred would there be sufficient quantities of quinolinic acid to be detectable by immunohistochemistry. IDO induction is the initial rate-limiting step in quinolinic acid production via the kynurenine pathway, and it is the only enzyme in the pathway inducible by interferon-γ (Werner-Felmayer et al., 1989). The concept of quinolinic acid as a mononuclear phagocyte secreted cytokine is supported by the observation that the microglial response to ischemia in hippocampus is obviated by pre-treatment with the NMDA receptor antagonist MK-801 (Streit et al., 1992), suggesting an NMDA agonist initiates the response. Thus, if infiltrating macrophages release quinolinic acid initially, microglia might act to upregulate the response by synthesizing and releasing additional quinolinic acid. Very little is known about the presence or absence of glutamate or quinolinate receptors on mononuclear phagocytes, but unusual glutamate-like receptors have been reported to be involved in monocyte chemotaxis (Malone et al., 1986). An analog of glutamate, 4-carboxylglutamate, was found to be an extremely potent chemotactic agent, while glutamate antagonized the response.

The production of antibodies to quinolinic acid was undertaken to further understanding into the cellular origins of the endogenous NMDA receptor agonist in the CNS under normal and pathological conditions. This initial report details the "basal" immunoreactivity observed in rats without overt immune stimulation. In the present study, no significant quinolinic acid immunoreactivity was observed in brain of unstimulated (non-symptomatic) rats. Strong quinolinic acid immunoreactivity was observed in numerous cells, however, in carbodiimide fixed spleen, lymph node, BALT, GALT, intestinal villi and thymus, while scattered cells were observed in lung alveoli, liver and skin. The specific localization of quinolinate positive cells within the spleen, thymus, lymph nodes and other lymphoid tissues supports a role for T-cell derived interferon-γ in the induction of quinolinic acid production. The present findings also suggest that quinolinic acid antibodies specifically recognize activated mononuclear phagocytes, and possibly other antigen presenting cells. These findings are consistent with a role for quinolinic acid in immune system function, rather than normal CNS function, and further implicate lymphoid derived cells in the production and release of quinolinic acid associated with various excitotoxic CNS pathologies.

The present antibodies may be generally used in diagnosing the extent of and in treating any disease which is manifested by QUIN-induced neuronal damage. For example, the present invention may be used to assess or alleviate excitotoxic damage caused by anoxic and ischemic brain damage, hypoglycemic brain damage, seizure-mediated brain damage, damage from Huntington's disease and Neurolathyrism, and even from complications with Alzheimer's disease. Further, this damage may be to any component of the nervous system, such as the brain, spinal cord or even peripheral nerves. It may also be used to prevent or minimize damage to neural implants in a mammalian host.

Prevention of damage to neural implants is important as such implants may play several roles, such as reconnecting of interrupted circuitry, increasing the quantity of neurotransmitter for existing activity, stimulating vascularization, removing toxic substances, promoting neuronal survival and growth via neurotropic interactions between host and transplant.

In general, there is a linear relationship between the degree of inflammation in the body, i.e. the sum total of all inflammatory processes in the body, and the level of QUIN in the blood. In accordance with the present invention. it has been discovered that the increase of QUIN concentration in mammalian blood is in proportion to the immune-stimulating capacity of the infections agent. For example, a rapid rise occurs when a potent stimulant is applied. Chronic or slow infections lead, instead, to slow increases or chronically high levels of QUIN in the blood of a patient.

Generally, when used to minimize, or even neutralize, damage from neurodegenerative diseases or to prevent damage to neural implants, the antibodies of the present invention may be administered by any conventional means of administering antibodies, and using concentrations which are sufficient to at least partially neutralize any QUIN present in the mammal.

As noted above, the present antibodies may be prepared by immunizing a suitable host with both protein-conjugated and gold particle-adsorbed QUIN. Polyclonal antisera obtained from the host are then affinity purified on a suitable gel coupled to QUIN.

Hapten-protein conjugates may be prepared with a coupling agent, such as carbodiimide and can be used to enhance the specificity of antibodies produced. The specificity of antibodies produced may be tested with nitrocellulose-immobilized protein conjugates and competitive ELISA methods.

In more detail, any standard carrier protein may be used which is routinely employed in immunizations, such as serum albumin, hemocyanin from horse shoe crabs or thyroglobulin from cows, for example. Further, antibody specificity may be enhanced by changing the carrier protein frequently, and by using gold particle-adsorbed QUIN immunizations. The latter appears to also improve the ability of the antibodies to bind free (soluble) QUIN.

Generally, the present antibodies have an affinity for QUIN such that less than i ng of protein having QUIN bound to the surface can be detected in a fluid sample.

The present antibodies may be used in the same capacity for either clinical or veterinary applications. In general, the level of QUIN in the blood is indicative of the degree of internal infection in any mammal. Further, the present antibodies may be used as a histopathological reagent for both animal and human biopsy specimens and in a kit for performing such analyses. Generally, any known method and kit therefor for detecting haptens may be modified in view of the disclosure herein for detecting QUIN.

EXAMPLE 2

Reagents were purchased from Sigma (Rockford, Ill.), immunochemicals from Vector (Burlingame, Calif.), and animals were required from Zivic-Miller (Allison Park, Pa.). The methods used for the production and characterization of the present antibodies are as described above.

A New Zealand white rabbit was immunized with both protein-conjugated and gold particle-adsorbed QUIN. The polyclonal antisera were affinity purified on an aminoalkylagarose based gel coupled with quinolinic acid. Several hapten-protein conjugates were prepared with carbodiimide as the coupling agent and were used for improving antibody specificity. Carbodiimide treated rat brain proteins were also prepared to block non-specific antibodies directed against protein epitopes. Nitrocellulose strips with a protein-hapten conjugates and treated brain proteins adsorbed to them were incubated with the primary antibodies to eliminate cross-reactivity. The protein conjugates were also serially diluted and spotted on nitrocellulose sheets to test the specificity of the antibodies by dot-blot assay.

Five albino Sprague-Dawley rats, weighing between 120 and 150 grams, were deeply anesthetized with Nembutal and perfused transcardially with 400 ml of an aqueous solution of 6% 1-ethyl-3(3-dimethylaminopropyl) carbodiimide hydrochloride at 37° C., containing 5% DMSO and 1 mM N-hydroxysuccinimide. The tissue was postfixed in 4% formaldehyde and cryoprotected by passage through 10%, 20% and 30% sucrose prior to freezing. Brains were sectioned in the frontal and horizontal planes, and spleens in cross-section, at a thickness of 20 µm.

Tissue sections were processed for immunohistochemistry by the free-floating method. Endogenous peroxidase was inhibited by incubating tissue sections with 0.3% $H_2O_2$ in methanol for 30 minutes, and sections were treated with 2% normal goat serum in phosphate buffered saline (2% NGS/PBS). Affinity and adsorption purified antibodies, diluted 1:300, or absorption-only purified antibodies diluted 1:10,000 in 2% NGS/PBS, were incubated with tissue sections overnight at room temperature with constant rotary agitation. Bound antibodies were visualized by the avidin-biotin-horse radish peroxidase complex method (Vectastain Elite) and developed with diaminobenzadine in urea peroxidase (Sigmafast tablets).

Antibody specificity was tested with nitrocellulose immobilized protein conjugates of a number of small molecules including picolinic, nicotinic, kynurenic, quinaldic, xanthurenic, and glutamic acids. After preadsorption of the affinity purified antibodies with picolinic, nicotinic and glutamic acid conjugates of BSA, less than 1% cross-reactivity was observed with any of the other small molecules coupled to BSA in dot-blot assays. Preadsorption of the antibody solutions with carbodiimide treated brain proteins practically eliminated background cross-reactivity in carbodiimide fixed brain and spleen tissue sections.

In more detail, the specificity of the present antibodies is described hereinbelow in greater detail.

Structurally similar compounds exhibiting $\leq 0.25\%$ cross-reactivity with the purified quinolinic acid antibody in a solid-phase enzyme assay system as listed below. All molecules were coupled to bovine serum albumin (BSA) by a carbodiimide reaction.

1-tryptophan
2-picolinic acid
3-nicotinic acid
4-kynurenic acid
5-kynurenine
6-quinaldic acid
7-xanthurenic acid
8-anthranilic acid
9-hydroxyanthranilic acid
10-glutamic acid
11-aspartic acid
12-gamma amino butyric acid
13-N-acetylaspartate
14-N-acetylaspartyglutamate
15-N-acetylglutamate
16-pyroglutamic acid The purified antibodies also do not interact with any native or carbodiimide treated proteins from brain tissue.

The purified antibody has been found to be cross-reactive to only one compound to date, phthalic acid, which is an almost identical dicarboxylic acid, lacking only the ring nitrogen. Phthalic acid is a synthetic compound used in organic syntheses, and is not found in animals. It may be present in some fungi. The antibody, as presently purified, cannot discriminate between these two compounds indicating that the ring nitrogen is not significantly involved in the antibody binding. However, this cross-reactivity with a synthetic compound not found in humans or animals will not present any complications to the use of this reagent.

Further, the present purified quinolinic acid antibodies will clearly label 5 nanograms of protein which has been conjugated with quinolinic acid via a carbodiimide reaction. Starting with 20 milligrams of protein and 10 milligrams of quinolinic acid, the carbodiimide reaction is continued at room temperature for 30 minutes. Utilizing other radiolabeled compounds, we have estimated that approximately 0.1% of the available quinolinic acid will be covalently attached to the protein carrier molecule under the conditions described in Moffett et al. 1993. This translates to a detectability limit of approximately 50 picograms of quinolinic acid bound to protein. Other structurally related compounds are not detectable when present in 500 fold excess over the concentration of quinolinic acid. The concentration of protein is given at the left, ranging from 2 micrograms of protein to 1 nanogram of protein. The compounds tested were, from left to right, quinolinic acid, kynurenic acid, nicotinic acid, picolinic acid, quinaldic acid, xanthurenic acid, glutamic acid, gamma amino butyric acid and tryptophan.

Application of the antibodies to carbodiimide fixed rat brain tissue from animals without observable pathology resulted in little or no quinolinic acid immunoreactivity. Very light immunoreactivity was observed in some circumventricular organs, ventricular linings, and meninges, but it was not significantly above background staining.

When carbodiimide fixed rat spleen tissue was stained with the affinity purified and preadsorbed antibodies, intense quinolinic acid immunoreactivity was observed in a population of cells occurring through the spleen. See FIG. 1. Staining in the spleen was variable from one animal to another, with some animals exhibiting large numbers of clustered and densely packed immunoreactive cells, and others displaying a more scattered distribution of stained cells. The immunoreactive cells were approximately 15 µm in diameter, and were highly variable in morphology. The greatest density of strongly immunoreactive cells was observed in the white pulp periarterial lymphocyte sheaths (PALS), especially at the edges of T-cell zones.

Very light, diffuse staining occurred within all B-lymphocyte follicles, defining them from the surrounding spleen tissue, but no such immunoreactivity occurred in T-cell regions, or within the red pulp. Follicular marginal zones appeared as unstained circular strips and contained variable numbers of heavily stained cells. Scattered, strongly immunoreactive cells were observed throughout the red pulp, but at significantly lower density than in the white pulp. Occasional clusters of moderately stained cells were observed within some follicular germinal centers. Quinolinate immunoreactivity was completely eliminated by incubation of the dilute primary antisera with 10 µg/ml of quinolinic acid conjugated BSA adsorbed to nitrocellulose. The immunoreactivity could not be blocked or reduced with the other conjugates in excess of 1 mg/ml.

The concentration of quinolinic acid in the brain increases dramatically as a result of widely disparate pathological phenomena. While the source of this neurotoxin is still a matter of debate, recent reports implicate macrophages or microglia as causative agents in quinolinic acid production and the resultant neuronal damage. Microglia have been shown to release a neurotoxic substance which acts through the NMDA type of glutamate receptor. An early study on the nature of a neurotoxin secreted by a mononuclear phagocytic cell line infected with HIV-1 indicated that the neurotoxin is a small (<2 kD), heat stable, protease resistant compound. However, that investigation failed to detect significant concentrations of quinolinic acid in the culture supernatants that displayed neurotoxic activity.

More recently, human peripheral blood macrophages were shown to produce substantial quantities of quinolinic acid in vitro and, moreover, γ-interferon was found to significantly increase conversion of tryptophan to quinolinic acid in these cells. Also, HIV-1 infection of these macrophages in vitro produced super-neurotoxic levels of QUIN in the culture medium.

It is known that IDO is the initial rate limiting enzyme leading to quinolinic acid production and its regulation plays an important role in controlling quinolinate synthesis. In macrophages, IDO is the only enzyme in the kynurenine pathway of tryptophan degradation which is known to be inducible by the action of γ-interferon. As noted above, γ-interferon increases the conversion of tryptophan to quinolinic acid by human macrophages, and this occurs by the induction of IDO in these cells. In poliovirus infected spinal cord, increased IDO expression is reported to have occurred only in macrophages and microglia within and around lesions, also implicating mononuclear phagocytes in the increased production of quinolinic acid. Macrophages and microglia, therefore, represent the most likely connection between γ-interferon induction of IDO, tryptophan degradation, and the increased quinolinic acid production observed in blood and CNS in response to infection or trauma.

No immunoreactivity was observed in microgila in the brains of control rats. Strong cellular immunoreactivity was quite limited in the present study, involving only a subpopulation of cells in the spleen, most concentrated within the PALS. Spleen macrophages are not typically found in higher numbers in the periarterial sheaths, suggesting that quinolinate positive spleen cells are a functional macrophage subpopulation, or that they include other cell types, such as dendritic cells. The selective staining of subpopulations of monocytic phagocytes could be explained if immunoreactivity were limited to monocytes at some stage during the process of activation. The stained cells would theoretically be those in which substantial IDO induction had occurred, since only they would contain sufficient quantities of quinolinic acid to be detectable by immunohistochemistry. It is noteworthy that the greatest densities of quinolinate immunoreactive cells were associated with T-cell zones, since T-lymphocytes release γ-interferon when stimulated. The lack of immunoreactivity observed in microglia in the present study should not be taken to indicate a lack of microglial involvement in pathological increases in brain quinolinic acid, since these cells can undergo a similar activation with the appropriate immune stimulation.

The dramatic responsiveness of the quinolinate production system to immune stimulation is attested to by the approximate 100–1,000 fold increase in the concentration of quinolinic acid in the cerebrospinal fluid of patients with inflammatory diseases, as compared to cases of non-inflammatory disease or controls. This high degree of inducibility is suggestive of an amplification system, perhaps involving monocyte recruitment or aggregation. The coupling of macrophage and microglial activation to quinolinic acid production implicates this NMDA receptor agonist in immune system signal transduction. Such coupling would require the presence of quinolinic acid receptors on the target cells in the immune and nervous systems. The identity of cells in the immune system which are responsive to quinolinic acid, and the nature of their responses, are in need of further investigation.

There is relatively little information on the possible presence of glutamate receptors on macrophages, microglia, or T and B lymphocytes. Unusual glutamate-like receptors have been reported associated with chemotaxis in mononuclear phagocytes. These cells responded chemotacticly to 4-carboxyglutamate, but this effect was antagonized by L-glutamate. From this, it appears that 4-carboxyglutamate binds to quinolinic acid receptors on these cells, and that glutamate acts as an antagonist at such receptors. In other studies, the microglial reaction to ischemia in hippocampus was reported to be blocked by the NMDA receptor antagonist MK-801, suggesting a role for glutamate receptors in microglial activation. These findings suggest that quinolinic acid is a chemotactic agent, cytokine or transmitter substance which is involved in macrophage-microglial signaling. This could occur during peripheral macrophage infiltration of the CNS, or in regions where the blood brain barrier was reduced. The potential activation of NMDA-like receptors on microglia by quinolinic acid might be expected to be coupled to calcium conductances and induction of chemotactic and phagocytic responses. In a similar fashion, the degree of peripheral infection could be monitored by the CNS if the level of quinolinic acid in blood acted as a signal from immune to neural systems in areas of the hypothalamus such as the median eminence or organum vasculosum lamina terminalis.

Thus, one aspect of the present invention pertains to a method of minimizing, or even neutralizing, damage to a mammal from QUIN due to neurodegenerative disorders. In accordance with this aspect of the present invention, any mammal, such as a human or even a dog, cat, horse, cow or pig may be treated. Further, any of these hosts may be so treated for any of the neurodegenerative disorders affecting them.

Generally, in using this aspect of the present invention, the amount of QUIN present in the fluid sample selected is determined. Then, an appropriate mass of the present antibodies is selected for administration to the mammal.

Any conventional method may be used to detect and measure the amount of QUIN present in the host mammal. However, the antibodies of the present invention may, themselves, be used to detect and measure the amount of QLA present.

Once the amount of QUIN has been determined, a sufficient quantity of the present antibodies are administered to at least partially neutralize the QUIN. Preferably, an amount is administered to completely neutralize the QUIN. In general, the present antibodies will be administered in an amount of about $10^3$ to about $10^7$ molecules/kg of body weight. However, this amount may vary depending upon the judgment of the attending physician. Further, the antibodies may be administered by intravenous, intraperitoneal or subcutaneous injection. Preferably, however, the antibodies are administered by slow infusion. For example, the antibodies may be administered in sterile 5% saline or dextrose-5%-saline using a concentration of about $10^3$ to $10^7$ antibody molecules per 250–2,500 µl.

The present invention also provides several diagnostic kits and methods for detecting QUIN using the present antibodies.

Additionally, the present invention also provides a method of detecting the presence of QUIN in mammals as a means of determining the existence of and the extent of internal infection and neurological disease. Further, the present invention provides a diagnostic kit for detecting QUIN in mammals.

In more detail, the antibodies of the present invention may be used to therapeutically detect and monitor the amount of QUIN in mammalian serum. Generally, any suitable means of detection may be used.

Generally, the test kit of the present invention is for the detection of QUIN in physiological fluids of a mammal. Further, it is preferred that a competitive ELISA or RIA type assay be used.

For example, by using the antibodies of the present invention, a test kit may be constructed analogous to that disclosed in U.S. Pat. No. 4,624,916, which is incorporated herein in the entirety.

In more detail, the present test kit for the detection of QUIN relies upon the use of a competitive assay, such as a radioimmunoassay (RIA) or enzyme-linked immunosorbant assay (ELISA) to detect QUIN using the present antibodies. Further, kits utilizing either of these methodologies are provided.

For example, a direct ELISA technique may be used. While direct ELISA is a standard and well known technique, the following procedure is offered for purposes of illustration and is not intended to be limitative.

EXAMPLE 3

Materials

QUIN analyte (antigen)-containing fluid sample.
Coating buffer
Diluting buffer
Wash buffer
Normal saline
Urease- or HRPO-IgG conjugate
Urease substrate solution or peroxidase substrate solution
Polyvinyl or polystyrene 96-well microliter plates
Multichannel pipet
Adhesive covers or tape for covering microliter plates
Microliter plate spectrophotometer with 590-nm and/or 405-nm filters.

The following general protocol may be used:

1. Dissolve QUIN- containing fluid sample and controls in coating buffer at –10 µg/ml.

Depending on the affinity of the particular antibody for the antigen, it may be necessary to increase the amount of antigen in coating buffer to about 100 µg/ml.

For specificity testing, closely related control antigens should be used which the QUIN- antibody should not recognize.

2. Fill columns 2 through 12 of a 96-well microliter plate with 0.05 ml coating buffer.

A 96-well plate is divided into 12 columns (labeled 1 to 12) and 8 rows (labeled A to H).

3. Starting in column 1 of a 96-well microliter plate, serially dilute antigen in coating buffer. Place 0.1 ml of antigen solution in each well in column 1. Remove 0.05 ml from each well with a multichannel pipet and transfer to each well in column 2, which contains 0.905 ml of coating buffer. Pipet material in column 2 five times up and down. Remove 0.05 ml from each well in column 2 and transfer to column 3. Repeat this procedure through column 11. Remove 0.05 ml and discard. Leave column 12 blank. Prepare two plates per antigen for duplicate assays. Repeat step 3 for controls.

This will give a range of dilutions in each of 8 rows (A to H) from 1:1 through 1:1,024, i.e., column number (dilution): 1 (1:1), 2 (1:2), 3 (1:4), 4 (1:8), 5 (1:16), 6 (1:32), 7 (1:64), 8 (1:256), 10 (1:512), and 11 (1:1,024).

4. Cover the plates with adhesive covers or tape and incubate overnight at 4° C. or 2 hr at 37° C.

Overnight coating generally gives more uniform results.

5. Remove antigen solution by shaking into a sink and fill all wells with 0.2 ml diluting buffer. Incubate for 1 hr at room temperature.

HRPO is inactivated by sodium azide. Do not use buffers containing sodium azide with HRPO-IgG conjugates. Filter sterilize buffers used routinely (i.e., diluting buffer) and store at 4° C.

6. Remove diluting buffer by shaking into a sink and then fill rows B to h with 0.05 ml diluting buffer.

7. Add 0.1 ml of enzyme-antigen specific antibody conjugate diluted in diluting buffer to row A of each plate. Recommended starting dilution of conjugate is 1:100. Serially dilute conjugate from row A to row H using the pipetting procedure described in step 3. Final volume of conjugate in each well should be 0.05 ml.

This will give a range of dilutions from 1:100 through 1:12,800, row (dilution): A (1:100), B(1:200), C (1:400), D(1:800), E (1:1,600), F (1:3,200), G (1:6,400), and H (1:12,800).

8. Cover the plate with adhesive covers or tape and incubate for a set length of time at a controlled temperature.

Time and temperature of incubation are determined empirically. Generally, 30 to 60 min at 37° C. is sufficient. Longer times of incubation may increase sensitivity, but nonspecific binding may also increase.

9. Shake out the plates into a sink. Wash plates with wash buffer twice for urease-IgG conjugates and four times for HRPO-IgG conjugates by filling well and shaking out the wash buffer into a sink. If an urease-antibody conjugate was used, rinse plates an additional three times with normal saline. pat plates dry by inverting on a paper towel.

10. Add 0.05 ml of either urease substrate solution or peroxidase substrate solution, depending on the enzyme-antibody conjugate used. Read absorbance at 590 nm (urease) or 405 nm (HRPO) using a microliter plate spectrophotometer.

11. Plot absorbance versus antigen concentration [Ag] on semilog paper for analysis of each dilution of enzyme-antibody conjugate. For working dilution of conjugate, choose a concentration that provides maximum sensitivity over a linear range of [Ag] and minimum binding (below 0.05 OD) to control antigens.

12. Prepare bacterial cell lysate antigens according to the support protocol on p. 11.2.7.

13. Serially dilute individual samples and control antigen preparations, as described in step 3, starting at approximately 10 µg/ml of antigen. Use two columns per sample.

14. Repeat steps 4 and 5.

15. shake out diluting buffer into a sink and 0.05 ml per well of enzyme-antibody conjugate diluted in diluting buffer at the concentration determined in step 11.

16. Cover the plates with adhesive covers and incubate 1 hr at 37° C.

17. Repeat steps 9 and 10.

18. Compare the absorbance of the sample to the standard curve (absorbance versus [Ag] plotted in step 11 in order to determine the quantity of antigen expressed per volume of fluid sample.

A specific example of a competitive ELISA methodology will now be provided.

EXAMPLE 4

Using a protocol similar to that given above in Example 3, a competitive ELISA was conducted for the quantitative analysis of QUIN in biological samples.

Polyalkaline phosphatase conjugated with QUIN (using a carbodiimide procedure) is used as the competing ligand. Primary antibody against QUIN is coated on the ELISA plate. Following blocking of the plate using 10% nonfat milk, different amounts of free QUIN (100 pg to 10 µg) are incubated with a fixed amount of the QUIN conjugated alkaline phosphatase in a total volume of 200 ul overnight (0°–4° C.). Following this incubation, the plates are washed and the bound alkaline phosphatase is quantitated by a color development procedure.

Figure 11:
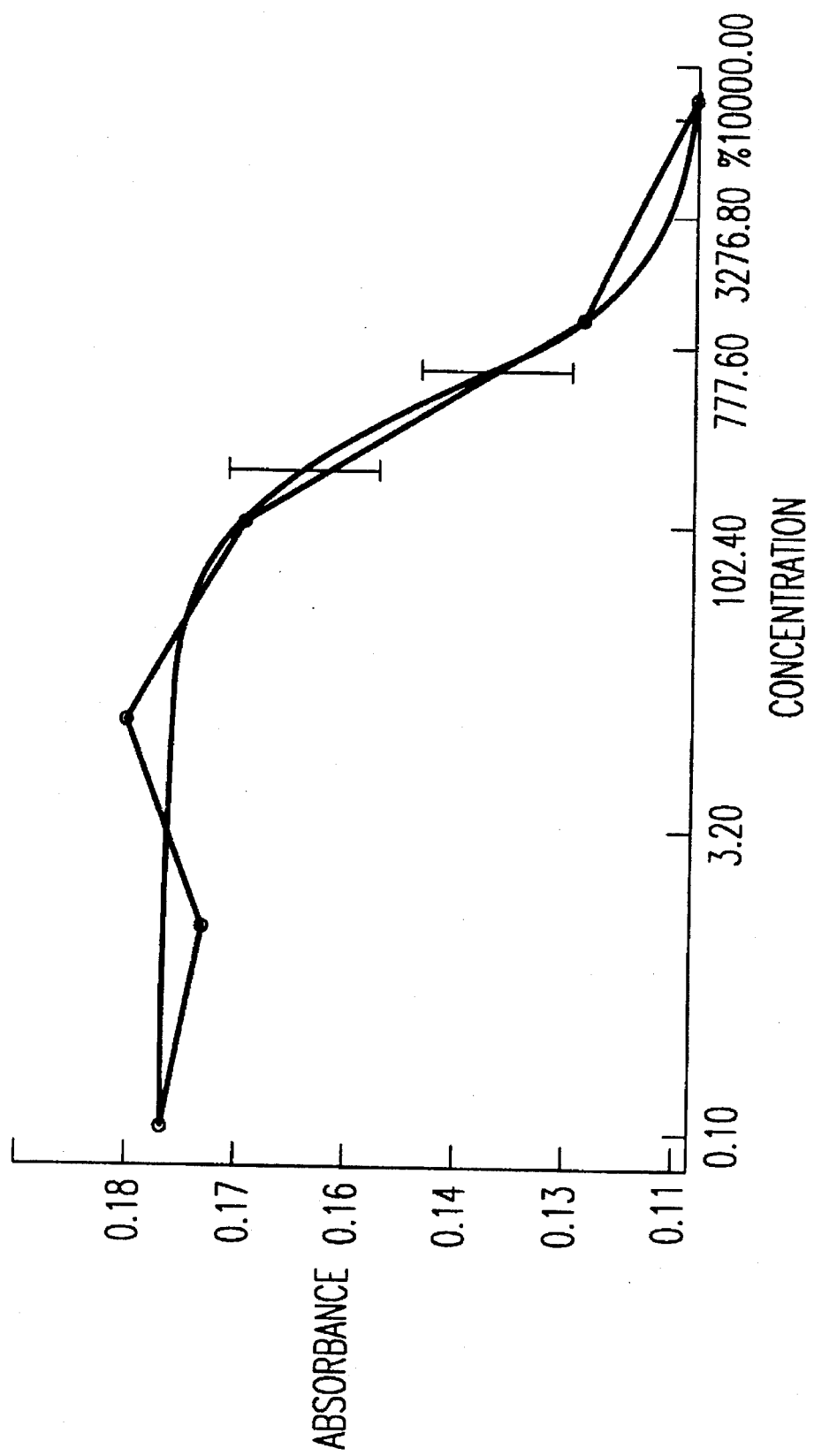
FIG. 11 illustrates a competitive ELISA plot of absorbance versus concentrations.

The results in FIG. 11 indicate that QUIN in the high nanogram to microgram range can be detected using this approach. However, this method needs to be optimized for use with biological samples as well as for improving the sensitivity of detection.

Generally, direct ELISA may be performed in a kit involving the binding of QUIN antigen directly to microliter wells. Antigen-specific antibody of an enzyme-antibody conjugate prepared by known methods binds to antigen bound to the microliter well surface. The conjugated enzyme cleaves a substrate to generate a colored reaction product that can be detected spectrophotometrically. The absorbance of the colored solution in individual microliter wells is proportional to the amount of antigen.

Generally, any assay or kit may be used as described in any of U.S. Pat. Nos. 4,230,805; 4,795,822; 4,772,697; 4,629,691; 4,608,252; 4,608,200; 4,605,754; 4,430,263; and 4,939,264, except that the antibodies of the present invention are used to detect QUIN analyte in a fluid sample.

Further, the ELISA kit of the present invention may be based upon a smaller number of microliters wells than described above. It is sufficient if the kits have as little as two or three QUIN standards for comparison with two fluid samples.

Immunohistopathological use of the Present Antibodies

Figure 10A:
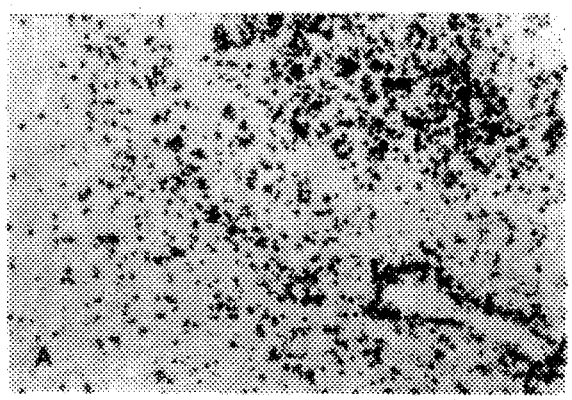
FIGS 10A and 10B illustrate two photomicrographs of QUIN-stained fixed brain sections from rats inoculated with two distinct types of brain tumor.
Figure 10B:
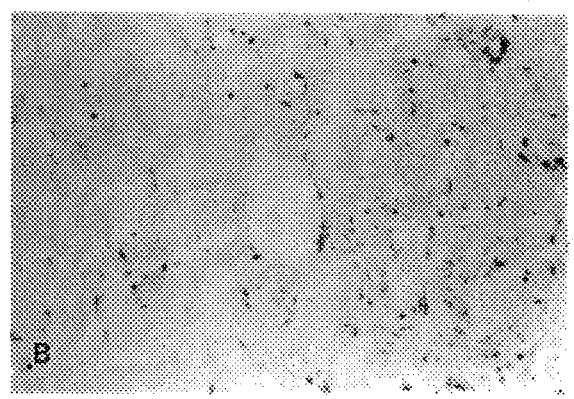

Purified polyclonal antibodies specific to quinolinic acid (QUIN) can be utilized on carbodiimide fixed tissue biopsies or specimens to determine the degree of infiltrating activated phagocytes. FIGS. 10A–10B show two photomicrographs of QUIN-stained fixed brain sections from rats inoculated with two distinct types of brain tumor. FIG. 10A depicts QUIN staining in the pyriform cortex of a rat which has been implanted with a glioma cell line (#F98), while FIG. 10B shows the staining observed in a neuroblastoma (#E367). The degree of activated immune cell infiltration is much more evident in the glioma (FIG. 10A) than in the neuroblastoma (FIG. 10B). Such differential staining may be found to be diagnostic of the type of tumor during the analysis of biopsy specimens. Magnification=120X.

Generally, any tissues of the body which contain cells producing QUIN may be fixed using the method described hereinabove for immunohistopathological studies. Such studies may be to determine the physiological location of QUIN production, the identity of the QUIN-producing cells as well as the extent of QUIN-production and of neurodepenerative disease.

In addition to the above, the present invention is predicated upon still further discoveries.

First, for the first time, QUIN antibodies have been used to demonstrate that in addition to macrophages, another type of mononuclear phagocyte, namely brain microglia, also produce QUIN when immunologically stimulated.

Moreover, by using the present antibodies, it has also been discovered that another type of immune cell type not previously thought to produce QUIN, namely dendritic cells, does, in fact, produce significant amounts of QUIN when stimulated. Examples of dendritic cells include Langerhans cells of the skin, interdigitating cells of lymphoid organ T-cell areas and follicular dendritic cells of lymphoid organ B-cell areas.

Other studies have found that several continuous cell lines will produce only very small amounts of QUIN when stimulated with γ-interferon, such as THP-1 monocyte cell line, 4937 monocyte cell line and SKHep1 cells of liver origin. To date, no other cell types have been found to produce QUIN.

In fact, the present inventors have found that when anti-QUIN antibodies are applied to the major tissues of rodents, only cells resembling macrophages, dendritic cells or microglia have been identified as the immunoreactive cells. Thus, it seems that only so-called antigen-presenting cells produce QUIN, and only after immune stimulation.

Thus, the present invention provides a method of detecting QUIN-presenting or producing cells by contacting a fixed tissue culture with the labelled antibodies of the present invention and detecting any QUIN-presenting or producing cells present. The means of labelling may be any standard radiological or flugescent methodology known to those skilled in the art. The fixing of the tissue culture may be in accordance with the techniques described in *methods in Enzymology*, vol. 70 "Immunological Techniques", Carbodiimides for Immunizing Conjugates, "The Use of Carbodiimides in the Preparation of Immunizing Conjugates", by S. Bauminger and M. Wilchek, pp.151-159; "The Use of Glutonaldehyde as Compiling Agent for Proteins and Peptides", by M. Reichlin, pp. 159-165; *Analytical Biochemistry*, 150, 220-222 (1986), "Enhancement by N-Hydroxysulfosuccinimide of Water-Soluble Carbodiimide-Mediated Compiling Reactions, Staros et al; and *Journal of Histochemistry and Cytochemistry*, vol. 41, No. 4, pp. 559-570 (1993), by Moffett et al, which are each incorporated herein by reference.

Further, the present invention generally provides a method of treating a mammal, particularly a human, suffering from physical trauma, wherein the trauma results in enhanced production of QUIN in the body. Such traumas may be pathological infection, stress by anoxia, cuts, bruises and even blunt force trauma. Generally, with any trauma, QUIN levels reach a general maximum level at about 20 to 30 hours, usually about 24 hours, after onset of trauma. Moreover, QUIN levels drop as the trauma subsides. In general, a "significant" increase in QUIN level will be about 50% increase over the background level. This background level may be determined by the artisan.

A notable exception to the above pattern, however, is Acquired Immuno-Deficiency Syndrome (AIDS). In accordance with another aspect of the present invention it has been discovered that the present antibodies may be used to inhibit or reduce AIDS-dementia symptoms.

Generally, therefore, the present invention provides a method of treating AIDS-dementia, which is characterized by a general neurological deterioration. This general neurological deterioration may be seduced or inhibited by administering an effective amount of the antibodies of the present invention to a mammal, particularly a human, suffering from AIDS-dementia.

In general, a patient suffering from AIDS is monitored for increases in QUIN level in blood or cerebrospinal fluid, and the antibodies of the present invention are administered at the direction of the attending physician.

Further, in applying the present invention to human therapy, which is to say, applying rabbit polyclonal antibodies against QUIN to humans, a conventional modification may be effected. Notably, the Fab fragment of the rabbit polyclonals produced may be isolated by any conventional methodology in order to reduce or eliminate the human immune response against the polyclonals without interfering with or reducing the affinity of the polyclonal antibodies for QUIN. Such methodologies are well known to those skilled in the art.

Further, since the QUIN-producing cells of the body produced enhanced amounts of QUIN generally in response to inflammation, by detecting the extent of QUIN production from these cells, by virtue of the present invention it is now also possible to directly assess the extent of inflammation or trauma in cells, as noted above. That is, certain cells, as described above, may be used for certain types of tissue.

Generally, Fab fragments may be generated using the procedure of Harlow and Lane, "Antibodies: A Laboratory Manual", Digesting Antibodies with papain to Isolate Fab Fragments, pp. 628-629, Cold Spring Harbor Laboratory, New York.

Finally, in accordance with the present invention, it is also now possible to induce a mammal, particularly a human, to procure endogenous antibodies by effecting immunization using gold adsorbed QUIN. Generally, gold-adsorbed QUIN is produced using the procedure described above, for example. This material is then administered in small quantities, such as on the order of 1-10 nanomoles in total amount. This will cause endogenous generation of QUIN-antibodies which may be used to provide a treatment for AIDS-dementia, i.e. to, perhaps, provide a more facile manner of producing antibodies, or to provide a preventive treatment for reducing or generally inhibiting the effect of enhanced QUIN-production in the body.

Generally, in any of the treatments afforded by the present invention, the amounts of antibodies administered will be the same.

Having described the present invention, it will now be apparent that many changes and modifications can be made to the above-described embodiments without departing from the spirit and the scope of the present invention.

What is claimed and desired to be secured by Letters Patent is:

1. A method of immunohistologically determining a level, location, or cellular source of quinolinic acid production in mammalian tissues which comprises:

a) obtaining a sample of one or more mammalian tissues or cells isolated therefrom, b) fixing said sample, c) contacting the fixed sample with polyclonal antibodies which are specific for quinolinic acid, thereby allowing said polyclonal antibodies to react with any quinolinic acid in said fixed sample, to form an antibody-quinolinic acid complex, and d) detecting said antibody-quinolinic acid complex in said fixed sample in order to determine the level, location, or cellular source of quinolinic acid production in said one or more mammalian tissues or cells isolated therefrom.

2. The method of claim 1, wherein said polyclonal antibodies have less than 0.25% cross-reactivity with another compound selected from the group consisting of picolinic acid, nicotinic acid, kynurenic acid, quinaldic acid, xanthurenic acid and glutamic acid.

3. The method of claim 1, wherein said polyclonal antibodies are labeled and specifically bind to and detect at least 50 picograms of quinolinic acid.

4. The method of claim 1, wherein said polyclonal antibodies are Fab antibody fragments.

5. The method of claim 1, wherein said one or more mammalian tissues are nervous tissue.

6. The method of claim 5, wherein said nervous tissue is selected from the group consisting of brain tissue, spinal cord tissue and peripheral nervous tissue.

7. The method of claim 1, wherein said one or more mammalian tissues are human tissues.

8. The method of claim 7, wherein said human tissues are nervous tissue.

9. The method of claim 8, wherein said nervous tissue is selected from the group consisting of brain tissue, spinal cord tissue and peripheral nervous tissue.

10. The method of claim 1, wherein the location of quinolinic acid production is determined.

11. The method of claim 1, wherein the cellular source of quinolinic acid production is determined by determining identity of cells in said sample producing quinolinic acid.

12. A method of immunohistologically determining inflammation in tissues of a mammal which comprises:
   a) obtaining a sample of one or more tissues from the mammal,
   b) fixing said sample,
   c) contacting the fixed sample with polyclonal antibodies which are specific for quinolinic acid, thereby allowing said polyclonal antibodies to react with any quinolinic acid in said fixed sample, to form an antibody-quinolinic acid complex, and
   d) detecting said antibody-quinolinic acid complex in said fixed sample in order to determine a level of quinolinic acid production in said one or more tissues from the mammal, a level of quinolinic acid production greater than that determined in normal fixed samples of the one or more tissues indicating inflammation in the one or more tissues of the mammal.

13. The method of claim 12, wherein said polyclonal antibodies have less than 0.25% cross-reactivity with another compound selected from the group consisting of picolinic acid, nicotinic acid, kynurenic acid, quinaldic acid, xanthurenic acid and glutamic acid.

14. The method of claim 12, wherein said polyclonal antibodies are labeled and specifically bind to and detect at least 50 picograms of quinolinic acid.

15. The method of claim 12, wherein said polyclonal antibodies are Fab antibody fragments.

16. The method of claim 12, wherein said mammal is a human.

* * * * *